(12) United States Patent
Rivera et al.

(10) Patent No.: US 6,423,845 B1
(45) Date of Patent: Jul. 23, 2002

(54) PROCESS AND INTERMEDIATES TO A TETRAHYDRO-[1,8]- NAPHTHYRIDINE

(75) Inventors: Nelo R. Rivera, Scotch Plains; Yi Xiao, Fanwood; Nobuyoshi Yasuda, Mountainside, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 15 days.

(21) Appl. No.: 09/718,139

(22) Filed: Nov. 21, 2000

Related U.S. Application Data

(60) Provisional application No. 60/167,260, filed on Nov. 22, 1999.

(51) Int. Cl.[7] .............................................. C07D 471/04
(52) U.S. Cl. ...................................................... 546/122
(58) Field of Search ........................................ 546/122

(56) References Cited

U.S. PATENT DOCUMENTS

| | | |
|---|---|---|
| 5,952,341 A | 9/1999 | Duggan et al. |
| 6,017,926 A | 1/2000 | Askew et al. |
| 6,048,861 A | 4/2000 | Askew et al. |

FOREIGN PATENT DOCUMENTS

| | | |
|---|---|---|
| WO | WO 98/18460 | 5/1998 |
| WO | WO 99/31061 | 6/1999 |
| WO | WO 99/31099 | 6/1999 |

OTHER PUBLICATIONS

Cheng et al., "The Friedländer Synthesis of Quinolines", Organic Reactions, vol. 28, pp. 37–201, (1982).

Weinreb et al., "Total Synthesis of the Antitumor Antibiotic Streptonigrin", J. Am. Chem. Soc., vol. 104, pp. 536–544, (1982).

*Primary Examiner*—Patricia L. Morris
(74) *Attorney, Agent, or Firm*—Philippe L. Durette; Melvin Winokur

(57) ABSTRACT

A novel process is provided for the preparation of 3-(5,6,7,8-tetrahydro-[1,8]-naphthyridin-2-yl)-propylamine which is useful in the synthesis of αv integrin receptor antagonists. Also provided are useful intermediates obtained from the process.

4 Claims, No Drawings

PROCESS AND INTERMEDIATES TO A TETRAHYDRO-[1,8]- NAPHTHYRIDINE

CROSS-REFERENCE TO RELATED APPLICATIONS

The present application claims priority of U.S. provisional application serial No. 60/167,260, filed Nov. 22, 1999, the content of which is hereby incorporated by reference.

FIELD OF THE INVENTION

The present invention discloses a novel process for the preparation of 3-(5,6,7,8-tetrahydro-[1,8]-naphthyridin-2-yl)-propylamine which is a useful intermediate in the synthesis of αv integrin receptor antagonists.

BACKGROUND OF THE INVENTION

The present invention provides an improved process for the preparation of 3-(5,6,7,8-tetrahydro-[1,8]-naphthyridin-2-yl)-propylamine (I).

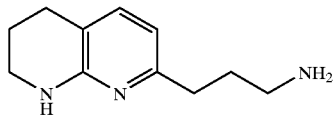

The present invention also provides intermediates useful in the disclosed process.

The synthesis of compound (I) has previously been disclosed in U.S. Pat. No. 6,048,861 (Apr. 11, 2000); U.S. Pat. No. 5,952,341 (Sep. 14, 1999); WO 98/18460; and WO 99/31061. In these prior art references, the naphthyridine ring is constructed by way of a Friedländer reaction between 2-amino-3-formyl-pyridine and either 5-(benzyloxycarbonylamino)-2-oxo-pentane or 5-(t-butyloxycarbonylamino)-2-oxo-pentane. These methods involve a total of six to eight chemical transformations, several chromatographic purifications, and an overall yield of about 38%.

In the present invention, compound (I) is efficiently produced via a novel regioselective Friedländer reaction between a β-ketophosphonate and 2-amino-3-formylpyridine in the presence of a base to afford the desired protected [1,8]-naphthyridine intermediate which can be readily converted in two steps into the final product (I).

SUMMARY OF THE INVENTION

This invention is concerned with a process for preparing 3-([5,6,7,8]-tetrahydro-[1,8]-naphthyridin-2-yl)-propylamine of structural formula (I) and certain useful intermediates obtained during that process. The process utilizes a novel Friedländer reaction to provide a protected 3-([1,8]-naphthyridin-2-yl)-propylamine intermediate, followed by partial hydrogenation, and removal of the amine protecting group PG or, alternatively, removal of the amine protecting group PG, then partial hydrogenation.

The novel process and novel intermediates are illustrated in the following embodiment denoted in Scheme 1 below.

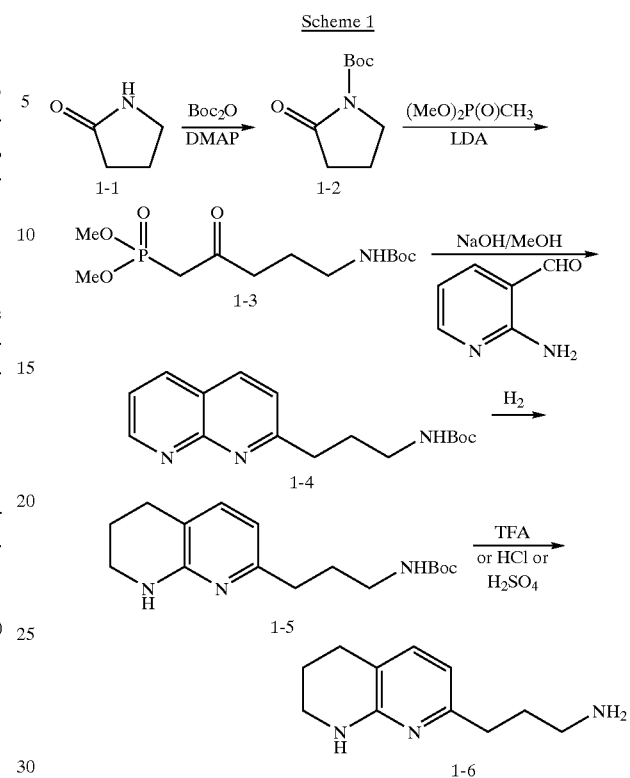

As disclosed in U.S. Pat. No. 6,048,861 (Apr. 11, 2000); U.S. Pat. No. 5,952,341 (Sep. 14, 1999); WO 98/18460; and WO 99/31061, compound (I) is a key intermediate in the synthesis of αv integrin receptor antagonists which are useful for inhibiting bone resorption and therefore treating and/or preventing osteoporosis.

DETAILED DESCRIPTION OF THE INVENTION

The process of the present invention involves the preparation of the compound of structural formula (I):

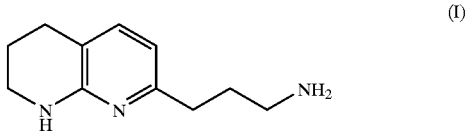

comprising the steps of:

(a) producing a compound of structural formula (II):

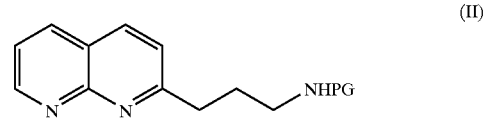

by treating 2-amino-3-formylpyridine with a compound of structural formula (III):

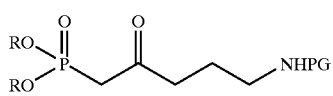

(III)

wherein PG is an amine protecting group and
R is $C_{1-4}$ alkyl or phenyl-$C_{0-2}$ alkyl;
in the presence of a base A in an organic solvent B, and isolating the resulting product (II).

The compound of structural formula (III) is produced by treating a protected pyrrolidone of structural formula (IV):

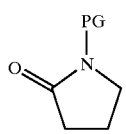

(IV)

with a methylphosphonate of structural formula (V):

(RO)₂P(O)CH₃   (V)

in the presence of a base C in an organic solvent D, and isolating the resulting product (III).

Compound (II) is converted into the final product (I) either by initial partial hydrogenation followed by cleavage of the amine protecting group PG (PATH A) or initial cleavage of the protecting group PG followed by partial hydrogenation (PATH B).

PATH A

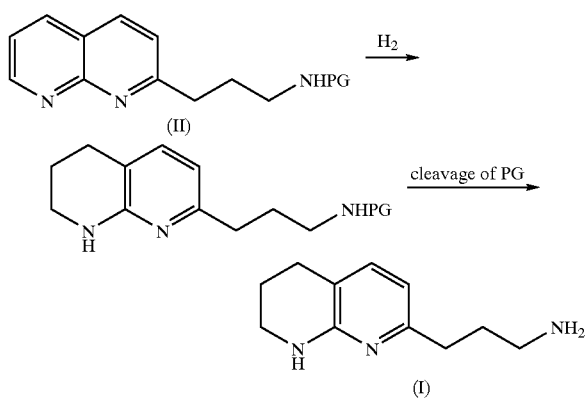

PATH B

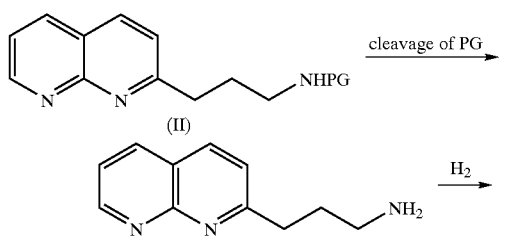

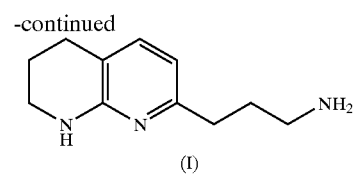

(I)

The key step in the process of the present invention is a novel regioselective Friedlander reaction of 2-amino-3-formylpyridine with the β-ketophosphonate Homer-Emmons reagent (III) in an organic solvent B in the presence of a base A to generate the corresponding anion. In one embodiment of the process, an alkali metal hydroxide, such as lithium, sodium, or potassium hydroxide, is used as the base A. However, other bases, such as an alkali metal alkoxide, for example, sodium methoxide, may also be used in the condensation reaction. The reaction is carried out in an organic solvent B, such as methanol, ethanol, isopropyl alcohol, methyl t-butyl ether (MTBE), THF, mixtures thereof, or aqueous organic solvent B. In one embodiment, the reaction solvent is methanol or aqueous methanol. In another embodiment, the R group of the β-ketophosphonate III is methyl. However, bulkier R groups, such as ethyl, isopropyl, or benzyl, may also be employed. The Friedlander reaction forms the desired protected naphthyridine intermediate (II) in a regioselective manner which can subsequently be processed into the final product (I) following the two-step sequence of PATH A or PATH B above. The β-ketophosphonate Horner-Emmons reagent (III) is derived by ring opening of appropriately protected pyrrolidone (IV) in an organic solvent D with the anion of the methylphosphonate (V) at a temperature range of about 0° C. to -80° C. obtained with a base C. In one embodiment of the present process, pyrrolidone is protected as a carbamate derivative, such as benzyl or t-butyl carbamate. Use of such a protecting group provides for its ready cleavage at the final or penultimate step either by treatment with acid in the case of t-butyl carbamate or by hydrogenolysis in the case of benzyl carbamate. In another embodiment of this step of the process, the anion of the methylphosphonate is generated with a base C, such as an alkali metal amide, for example, lithium diisopropylamide (LDA), an alkyl lithium, for example, butyl or hexyl lithium, or an alkali metal hexamethyldisilazide, for example, lithium or potassium hexamethyldisilazide. In another embodiment of the process of the present invention, the organic solvent D is selected from the group consisting of diethyl ether, 1,4-dioxane, 1,2-dimethoxyethane (DME), methyl t-butyl ether (MTBE), diglyme, THF, toluene, dichloromethane, NMP, DMF, DMPU, and mixtures thereof. In yet a further embodiment of the ring-opening reaction, the methylphosphonate is used in an amount of 1.0 to 2.0 molar equivalents of the protected pyrrolidone.

2-Pyrrolidone is protected following standard conditions, such as those described in *J Org. Chem.*, 1983, 48, 2424, for the t-butyloxycarbonyl (Boc) derivative. N-Boc-pyrrolidone (1—1) can also be prepared in near quantitative fashion by treating pyrrolidone with one molar equivalent of Boc anhydride neat in the presence of 0.2 mol % of DMAP at room temperature.

Following PATH A, the compound of structural formula (II) is converted into the final product (I) by partial hydrogenation in an organic solvent, such as a lower alkanol, including methanol, ethanol, and isopropanol, THF, MTBE, ethyl acetate, isopropyl acetate, or aqueous organic solvent, in the presence of a noble metal catalyst such as rhodium-on-carbon at or about atmospheric pressure until hydrogen uptake ceases. Other catalysts which can be employed in the hydrogenation reaction include Pd/C, Ru/C, Pd/Al$_2$O$_3$, Pt/C, PtO$_2$, Pt/Al$_2$O$_3$, Raney nickel, Rh/Al$_2$O$_3$, and Ru/Al$_2$O$_3$. The final step is cleagage of the amine protecting group PG. When the amine protecting group is t-butyloxycarbonyl, it may be cleaved by treatment with trifluoroacetic acid, sulfuric acid, HCl in ethyl acetate, HCl in diethyl ether, or HCl in dioxane. Other protecting groups are removed by standard literature conditions, such as those found in T. W. Greene and P. G. M. Wuts, *Protective Groups in Organic Synthesis*, 2$^{nd}$ Edition (1991).

Following PATH B, the step of cleaving the amine protecting group PG is first carried out and is followed by the step of partial hydrogenation using the conditions described in the previous paragraph.

A further embodiment of this invention comprises the following novel compounds of structural formula (VI) which are intermediates in the present novel process for preparation of compound (I):

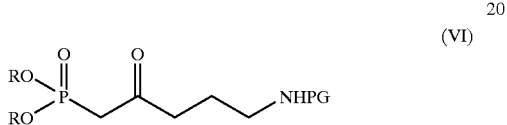

(VI)

wherein PG is an amine protecting group and R is C$_{1-4}$ alkyl or phenyl-C$_{0-2}$ alkyl. In class of this embodiment, PG is t-butyloxycarbonyl or benzyloxycarbonyl and R is methyl.

Representative experimental procedures utilizing the novel process are detailed below. For purposes of illustration, the following Example is directed to the preparation of compound (I), but doing so is not intended to limit the process of the present invention to the specific conditions for making the compound.

Abbreviations: Boc is t-butyloxycarbonyl; CH$_2$Cl$_2$ is dichloromethane; DMAP is 4-dimethylaminopyridine; EtOAc is ethyl acetate; Et$_3$N is triethylamine; K$_2$CO$_3$ is potassium carbonate; LDA is lithium diusopropylamide; MgSO4 is magnesium sulfate; MTBE is methyl t-butyl ether; NMR is nuclear magnetic resonance; Na$_2$CO$_3$ is sodium carbonate; NaHCO$_3$ is sodium hydrogencarbonate; and THF is tetrahydrofuran.

EXAMPLE 3-(5,6,7,8-Tetrahydro-[1,8]-naphthyridin-2-yl)-propylamine (1–6)

Step A: Preparation of N-Boc-pyrrolidone (1–2)

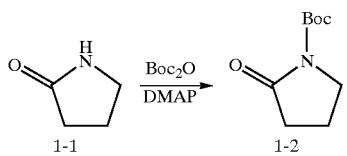

To a mixture of 2-pyrrolidone (1—1; 33.8 mL; 444 mmol) and Boc anhydride (97.0 g; 444 mmol) was added 4-dimethylaminopyridine (DMAP) (92 mg) and the mixture was stirred at 25–27° C. overnight in a water bath. After the reaction was complete, the mixture was distilled at 40 mmHg, keeping the same volume by addition of toluene (100 mL). No tert-butanol was detected by gas chromatography and $^1$H NMR. The solution (86.0 g) contained 1–2 with 7.6 wt % of toluene; 92.4 wt % purity; and 97% yield. The solution was used in the next reaction without any further treatment.

$^1$H NMR (400 MHz; CDCl$_3$): δ 3.72 (t, J=7.2 Hz, 2H), 2.48 (t, J=8.1 Hz, 2H), 1.97 (quintet, J=7.5 Ha, 2H), and 1.50 (s, 9H); $^{13}$C NMR (100 MHz, CDCl$_3$): δ 174.2, 150.1, 82.6, 46.3, 32.8, 27.9, and 17.3.

Step B: Preparation of 5-(t-butyloxycarbonylamino)-1-dimethylphosphonyl-2-oxo-pentane (1–3)

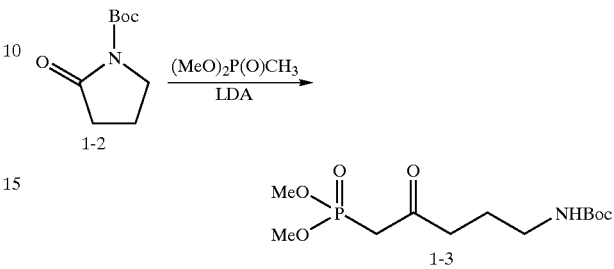

To a solution of diusopropylamine (50.6 mL) in dry THF (480 MnL) was added hexyllithium (2.5 M in hexanes; 125 mL) below –10° C. After aging for 30 min, a solution of dimethyl methylphosphonate (40.1 mL) in dry THF (128 InL) was slowly added to the reaction mixture while maintaining –60° C. After aging for 1 hour at –60° C., a solution of Boc-pyrrolidone (1–2) (50.0 g; 95 wt %) in dry THF (32 mL) was slowly added to the mixture, while maintaining the reaction temperature below –58° C. The solution was stirred at –60° C. for 1 hour and then at –40° C. for 1 hour. To the solution was added sulfiric acid (4 M; 167 mL). The mixture was allowed to warm up to 0° C. The organic layer was separated and concentrated in vacuo. The residue was dissolved in methanol (150 mL) and used in the next reaction without further purification. The isolated yield was 80%. An authentic sample was obtained by silica gel column chromatography.

$^1$H NMR (400 MHz, CDCl$_3$): δ 5.05 (broad s, 1H), 3.62 (d, J$_{H-P}$=11.2 Hz, 6H), 2.96 (d, J$_{H-P}$=22.0 Hz, 2H), 3.00–2.90 (m, 2H), 2.51 (t, J=7.0 Hz, 2H), 1.60 (quintet, J=6.8 Hz, 2H), 1.26 (s, 9H). $^{13}$C NMR (101 MHz, CDCl$_3$): δd 23.1, 27.7, 38.8, 40.3, 40.6 (d, J$_{C-P}$=127.7 Hz), 52.3 (d, J$_{C-P}$=6.4 Hz), 77.9, 155.5, 200.9 (d, J$_{C-P}$=6.0 Hz).

Step C: Preparation of (3-[1,8]-naphthyridin-2-yl)-N-Boc-propylamine (1–4)

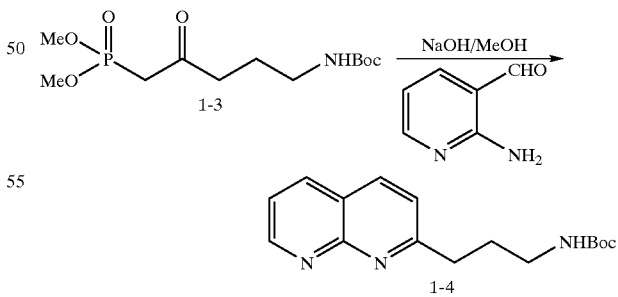

To a solution of 2-amino-3-formylpyridine (21.8 g) and β-keto phosphonate (1–3; 77.5 g; 95 wt %) in methanol (400 mL) was added aqueous sodium hydroxide (50 wt %; 13.7 mL). The mixture was stirred at 40–50° C. for 30 min. Additional 2-amino-3-formylpyridine (5.4 g) was added to the mixture with 100 mL of methanol. The mixture was stirred at 40–50° C. overnight and then concentrated in vacuo. The residue was dissolved in a mixture of ethyl acetate (270 mL) and water (135 mL). The organic layer was washed with water (150 mL) and concentrated in vacuo. The residue was dissolved in methanol (300 mL) and used in next step without further purification. The isolated yield was 90%. An authentic sample was obtained by silica gel column chromatography.

¹H NMR (400 MHz, CDCl₃): δ 8.98 (dd, J=4.2 and 2.0 Hz, 1H), 8.07 (dd, J=8.1 and 2.0 Hz, 1H), 8.01 (d, J=8.3 Hz, 1H), 7.35 (dd, J=8.1 and 4.2 Hz, 1H), 7.31 (d,J =8.3 Hz, 1H), 4.93 (broad s, 1H), 3.15 (quartet, J=6.5 Hz, 2H), 3.00 (t, J=7.6 Hz, 2H), 2.03 (quintet, J=7.2 Hz, 2H), and 1.34 (s, 9H); ¹³C NMR (101 MHz, CDCl₃): δ165.7, 155.9, 155.7, 153.1, 137.0, 136.7, 122.5, 121.4, 120.9, 78.7, 39.9, 36.1, 29.1, and 28.3.

Step D: Preparation of 3-(5,6,7,8-tetrahydro-[1,8]-naphthyridin-2-yl)-N-Boc-propylamine (1–5)

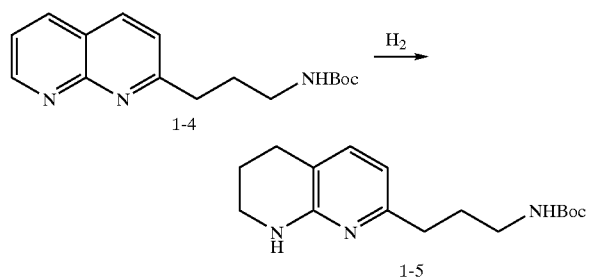

A solution of naphthyridine 1–4 (2.72 g) in methanol (20 mL) was hydrogenated in the presence of 5% rhodium on carbon (2.1 g; containing 63% of water) under 40 psi of hydrogen at 5° C. for 10 hours. The catalyst was filtered through Solka Flok and washed with methanol (25 mL twice). The filtrate and washings were combined, concentrated in vacuo, and dissolved in methanol (6.8 mL). To the solution was added water (6.8 mL) slowly at ambient temperature. The resulting solid was collected by filtration, washed with a mixture of water and methanol (2:1; 5 mL), and dried under vacuum to give the desired crystalline tetrahydronaphthyridine 1–5 (1.9 g). The mother liquor yielded an additional 5% of 1–5; m.p. 95.2–96.3° C.

¹H NMR (400 MHz; CDCl₃): δ 7.05 (d, J=7.4 Hz, 1H), 6.33 (d, J=7.3 Hz, 1H), 5.45 (bs, 1H), 4.92 (bs, 1H), 3.39 (m, 2H), 114 (s, 9H); J=7.3, 2H), 1.89 (m, 2H), 1.83 (m, 2H), 1.44 (s, 9H); ¹³C NMR (101 MHz; CDCl₃): δ157.1, 156.0, 155.4, 136.7, 113.4, 111.3, 78.6, 41.4, 40.3, 35.0, 29.4, 28.4, 26.2, 21.3.

Step E: 3-(5,6,7,8-Tetrahydro-[1,8]-naphthyridin-2-yl)-propylamine (1–6)

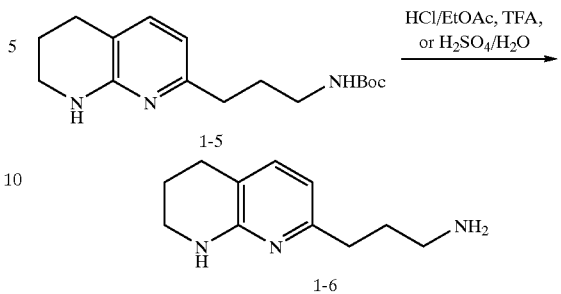

The title compound was prepared by treating the Boc derivative 1–5 with either HCl gas in ethyl acetate as described in U.S. Pat. No. 5,952,341 and WO 99/31061, or with trifluoroacetic acid in methylene chloride, or aqueous sulfuric acid; m.p. 66.0–68.5° C.

What is claimed is:

1. A process for preparing a compound of structural formula (HI):

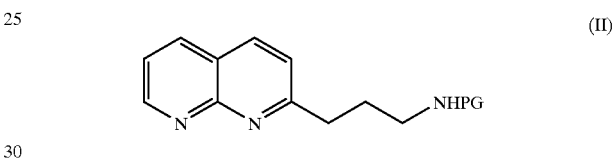

comprising the step of treating 2-amino-3-formyl-pyridine with a compound of structural formula (III):

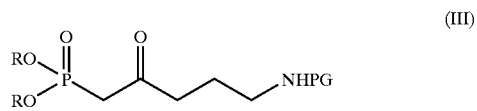

wherein PG is an amine protecting group and
R is C₁₋₄ alkyl or phenyl-C₀₋₂ alkyl;
in the presence of a base A in an organic solvent B, and isolating the resulting product (II).

2. The process of claim 1 wherein PG is t-butyloxycarbonyl or benzyloxycarbonyl.

3. The process of claim 1 wherein the base A is an alkali metal hydroxide or an alkali metal alkoxide.

4. The process of claim 3 wherein the alkali metal hydroxide is sodium or potassium hydroxide.

* * * * *